US008053217B2

(12) United States Patent
Berglund et al.

(10) Patent No.: US 8,053,217 B2
(45) Date of Patent: Nov. 8, 2011

(54) METHOD FOR PRODUCING ERITADENINE IN LIQUID PHASE FERMENTATION

(75) Inventors: Kris Arvid Berglund, Lulea (SE); Ulrika Rova, Boden (SE); Josefine Enman, Lulea (SE)

(73) Assignee: Working Bugs AB, Lulea (SE)

( * ) Notice: Subject to any disclaimer, the term of this patent is extended or adjusted under 35 U.S.C. 154(b) by 0 days.

(21) Appl. No.: 12/599,144

(22) PCT Filed: May 6, 2008

(86) PCT No.: PCT/SE2008/050516
§ 371 (c)(1),
(2), (4) Date: Jan. 22, 2010

(87) PCT Pub. No.: WO2008/136753
PCT Pub. Date: Nov. 13, 2008

(65) Prior Publication Data
US 2010/0221794 A1    Sep. 2, 2010

Related U.S. Application Data

(60) Provisional application No. 60/916,308, filed on May 7, 2007.

(51) Int. Cl.
C12P 17/18 (2006.01)
C07D 473/34 (2006.01)
C12N 1/14 (2006.01)
(52) U.S. Cl. .................. 435/119; 544/277; 435/254.1
(58) Field of Classification Search .................. 435/119, 435/254.1; 544/277
See application file for complete search history.

(56) References Cited

FOREIGN PATENT DOCUMENTS
EP    0 191 607 A2    8/1986

OTHER PUBLICATIONS

Lelik et al., "Production of the mycelium of shiitake (Lentinus edodes) mushroom and investigation of its bioactive compounds," 26(3):271-277, 1997.*
Hassegawa, R. et al., "Growth and antibacterial activity of Lentinula edodes in liguid media supplemented with agricultural wastes," Journal of Biotechnology, Issue of Aug. 15, Accepted Mar. 15, 2005, vol. 8, No. 2, p. 212-217.
Enman, J. et al, "Production of the Bioactive Compound Eritadenine by Submerged Cultivation of Shiitake (Lentinus edodes) Mycelia," J. Agric. Food Chem., 2008, vol. 56, pp. 2609-2612.
Kabir, Y.et al, "Dietary Mushrooms Reduce Blood-Pressure in Spontaneously Hypertensive Rats" (SHR). J. Nutr. Sci. Vitaminol. 1989, vol. 35, No. 1, pp. 91-94.
Kabir, Y. et al, "Effect of shiitake (Lentinus edodes) and maitake (Grifola frondosa) mushrooms on blood pressure and plasma lipids of spontaneously hypertensive rats," J. Nutr. Sci. Vitaminol. 1987, vol. 33, No. 5, pp. 341-346.
Kaneda, T. et al, "Effect of various mushroom preparations on cholesterol levels in rats," J. Nutr. 1966, vol. 90, pp. 371-376.
Suzuki, S. et al, "Influence of shiitake (Lentinus edodes) on human serum cholesterol," Mushroom Sci. 1974, vol. 9, 463-467.
Chibata, I. et al, "Lentinacin: a new hypocholesterolemic substance in Lentinus edodes". Experientia 25/12, 1969, 1237-1238.
Kamiya, T. et al, "Structure and syn-thesis of lentysine, a new hypocholesterolemic substance," Tetrahedron Letters 1969, vol. 10, No. 53, pp. 4729-4732.
Tokita, F. et al, "Isolation and chemical structure of the plasma-cholesterol reducing substances from shiitake mushroom," Mushroom Sci. 1972, vol. 8, pp. 783-787.
Rokujo, T. et al, "Lentysine: a new hypolipidemic agent from a mushroom," Life Sci. 1970, vol. 9, pp. 379-385.
Shimada, Y. et al, "Eritadenine-induced alterations of plasma lipoprotein lipid concentrations and phosphatidylcholine molecular species profile in rats fed cholesterol-free and cholesterol-enriched diets," Biosci. Biotechnol. Biochem. 2003, vol. 67, pp. 996-1006.
Shimada, Y. et al, "Dietary eritadenine and ethanolamine depress fatty acid desaturase activities by increasing liver microsomal phosphatidylethanolamine in rats," J. Nutr. 2003, vol. 133, pp. 758-765.
Shimada, Y. et al, "Effects of dietary eritadenine on the liver microsomal Δ 6-desaturase activity and its mRNA in rats," Biosci. Biotechnol. Biochem., 2003, vol. 67, pp. 1258-1266.
Sugiyama, K. et al, "Eritadenine-induced alteration of hepatic phospholipid-metabolism in relation to its hypocholes-terolemic action in rats," J. Nutr. Biochem. 1995, vol. 6, pp. 80-87.
Sugiyama, K. et al, "Dietary eritadenine modifies plasma phosphatidylcholine molecular species profile in rats fed different types of fat". J. Nutr. 1997, vol. 127, 593-599.
Takashima, K. et al, "The hypocho-lesterolemic action of eritadenine in the rat," Atherosclerosis. 1973, vol. 17, pp. 491-502.
Takashima, K. et al, "Effect of eritadenine on cholesterol metabolism in the rat," Biochem. Phar-macol. 1974, vol. 23, pp. 433-438.
Votruba, I. et al, "Eritadenine—novel type of potent inhibitors of S-adenosyl-L-homocysteine hydrolase," Collect. Czech. Chem. Commun. 1982, vol. 47, pp. 167-172.
Schanche, J. et al, "The effect of aliphatic adenine analogues on S-adenosylhomocysteine and S-adenosylhomocysteine hydrolase in intact rat hepatocytes," Mol. Pharma-col. 1984, vol. 26, pp. 553-558.
Saito, M. et al, "Quantitative analyses of eri-tadenine in shiitake mushroom and other edible fungi," J. Jap. Soc. Food Nutr. 1975, vol. 28, pp. 503-513. (English abstract).
Vitanyi, G. et al, "Detection of eritadenine in extracts from shii-take mushroom by gas chromatography mass spectrometry," Rapid Commun. Mass Spectrom. 1998, vol. 12, pp. 120-122.
Enman, J. et al, "Quantification of the bioac-tive compound eritadenine in selected strains of shiitake mushroom (Lentinus edodes)", J. Agric. Food. Chem. 2007, vol. 55, No. 4, pp. 1177-1180.
Leonard, N. J. et al, "5-amino-5-deoxyribose deriva-tives. Synthesis and use in the preparation of reversed nucleosides", J. Heterocycl. Chem. 1966, vol. 3, pp. 485-489.
Levene, P. A. et al, "Acetone Derivatives of d-Ribose," J. Biol. Chem. 1934, vol. 106, pp. 421-429.
Kawazu, M. et al, "Studies on the oxidation of reversed nucleosides in oxygen. I. Synthesis of eritadenine and its derivatives," J. Organ.. Chem. 1973, vol. 38, pp. 2887-2890.

* cited by examiner

Primary Examiner — Rosanne Kosson
(74) Attorney, Agent, or Firm — Venable LLP; Nancy J. Axelrod; Keith G. Haddaway

(57) ABSTRACT

Method to produce eritadenine by liquid phase fermentation of Lentinus edodes without formation of the fruit body wherein the Lentinus edodes is exposed to shear during its cultivation.

6 Claims, No Drawings

METHOD FOR PRODUCING ERITADENINE IN LIQUID PHASE FERMENTATION

BACKGROUND OF THE INVENTION

There is a significant industrial interest in the production of the compound eritadenine, particularly for but not limited to, its potential use as a blood cholesterol reducing therapeutic agent for humans. The fungus *Lentinus edodes*, more commonly known as the shiitake mushroom, is known to produce eritadenine when the fungus forms the fruit body of the mushroom. In prior art it was discussed that eritadenine could only be formed in significant amounts by causing the formation of the fruit body. This is a problem since the cost of raising shiitake solely for extraction of the eritadenine is prohibitive. In order to produce the eritadenine as a therapeutic agent there is a need to be able to produce it in fermentive culture.

SUMMARY OF THE INVENTION

The present invention provides a solution to the problem of producing eritadenine in liquid phase fermentation of *Lentinus edodes* without formation of the fruit body. In particular, the present invention provides a solution to the problem above by exposing the fungus to shear during its cultivation, it not only produces eritadenine, but also secretes it extracellularly into the fermentation medium. Thus, the new method disclosed in the present invention makes liquid phase fermentation a viable method for industrial eritiadenine production.

The invention discloses a method for producing eritadenine in liquid phase fermentation of *Lentinus edodes* herein the *Lentinus edodes* is exposed to shear during its cultivation.

Further example is the method above wherein *Lentinus edodes* also secretes eritadenine extracellularly into the fermentation medium.

The shear is in the order of a stirring rate of about at least 25 rpm.

The pH is in the range of about 3.0-6.0, preferably 4.0-5.0.

It is important to maintain a filamentous structure and not allow the organism to form a pellet structure. The shear accomplishes this.

Analogous, mutated variants thereof and derivate of *Lentinus edodes* could be used and is within the scope of the present invention.

The shiitake mushroom (*Lentinus edodes*) is traditionally used in East Asia, but ever since the last decades it is cultivated and consumed worldwide. In addition to being a popular edible fungus, it is well established as a medicinal mushroom since it contains several substances promoting health. Among other things, the ability to reduce blood cholesterol in both animals and humans has been ascribed to this mushroom (1-4). The agent responsible for the plasma cholesterol reducing effect is an adenine derivative designated as eritadenine (Eritadenine was designated as lentinacin or lentysine by the research groups initially isolating it, before given its trivial name.), 2(R),3(R)-dihydroxy-4-(9-adenyl)-butyric acid (5, 6), and its hypocholesterolemic effects has been shown in several studies on rats (5, 7-15). The hypocholesterolemic action of eritadenine has been investigated in several studies on rats, but the mechanism by which eritadenine bring about its hypocholesterolemic effect is not fully elucidated. Eritadenine is suggested to accelerate the removal of blood cholesterol either by stimulated tissue uptake or by inhibited tissue release; there are no indications of this compound inhibiting the biosynthesis of cholesterol (15) and the hepatic cholesterol levels in rats are not lowered by eritadenine (8, 15). Further, it has been shown that plasma cholesterol levels are significantly decreased in rats fed 0.005% of eritadenine in their diets (5, 9, 13, 14) and that the hypocholesterolemic action is caused by a decrease of the phosphatidylcholine (PC)/phophatidylethanolamine (PE) ratio (9-13). Eritadenine is a very potent inhibitor of the enzyme S-adenosyl-L-homocysteine hydrolase in rat liver cells (16) hereby causing an increase in the S-adenosylhomocysteine concentration (17). The increase in S-adenosylhomocysteine concentration in turn inhibits the PE N-methylation, thus increasing the PE content in liver microsomes (12). Further studies on rats suggest that eritadenine may increase the uptake of plasma lipoprotein cholesterol by the liver and thus reduce the plasma cholesterol (13). There is a possibility that the change in composition of the membrane phospholipids may activate lipoprotein receptors in liver cell membranes, thus regulating the uptake of plasma lipoprotein lipids (9).

The amounts of eritadenine in the fruit bodies of shiitake, as determined by column chromatography fractionation or GC, were found to be in the range 0.5-0.7 and 0.3-0.4 mg/g dried caps and stems, respectively (18, 19). Later studies pertaining to HPLC analysis of extracts from different fruit bodies of shiitake have shown eritadenine amounts in the range 3.17-6.33 mg/g mushrooms (20). The mycelia of shiitake have also been found to contain eritadenine; the amount determined by GC analysis was 0.737 mg/g dried biomass (21). Although fruit bodies seem to contain significantly higher amounts of eritadenine, growing fruit bodies of shiitake is a fairly demanding and time consuming process. Hence, in search for a source of eritadenine, mycelia could be an alternative to the fruit bodies.

The use of fungi for their biochemical activities is not a new phenomenon and in the later decades submerged cultivations of fungi for production of commercially important products have increased. Filamentous fungi, like shiitake, are morphologically complex organisms and exhibit different hyphal morphologies in submerged culture and thus differences in metabolism and production of secondary metabolites, such as eritadenine. The morphology of filamentous fungi in liquid culture is a result of the organism used and the chemical and physical culturing conditions, and it can range from freely dispersed filaments to densely interwoven aggregates. There is no generally preferred mycelial structure; which morphology is desirable for maximal yield depends on the product in question. The reason why shiitake mushrooms synthesize eritadenine is yet not clarified; i.e. the purpose this compound serves for the mushroom as well as the circumstances for its production is not elucidated. Therefore it is of great interest to investigate shiitake mycelia for eritadenine production; submerged cultivation of mycelia offers a convenient way to change the conditions in order to improve eritadenine yield and productivity. Hence, stirring rate and pH, two major factors influencing the morphology and probably eritadenine production, were investigated in the present invention.

Further, no data investing the broth from liquid cultures of shiitake mycelia for eritadenine content has been found in the literature. Eritadenine produced by submerged cultivation of shiitake mycelia could be an efficient process and if the compound of interest is excreted to the medium its availability increases and thus the convenience of harvesting. Therefore, the goal of the present invention was to evaluate if submerged cultivation of shiitake mycelia could be a conceivable way of producing eritadenine. The mycelia were cultivated under different conditions and both the biomass and culture broth were investigated for its eritadenine content.

DETAILED DESCRIPTION OF THE INVENTION

Results and Discussion

In search for a potential source of the blood cholesterol lowering compound eritadenine, as an alternative to fruit bodies of shiitake, its mycelia were investigated. Filamentous fungi, like shiitake, exhibit different hyphal morphologies in submerged cultures, depending on the cultivation conditions. The metabolism and production of secondary metabolites, such as eritadenine, might in turn be affected by the morphology of the mycelia. For this reason, the mycelia were cultivated in different conditions in order to investigate the effect of pH and stirring rate on production of eritadenine. The reason and circumstances for shiitake to produce eritadenine is not known, and there exists no data in the literature on its content in the broth from submerged cultivation. Therefore, not only the mycelia but also the resulting broths were analyzed for eritadenine content. In this study eritadenine was found in both the mycelia and the surrounding media, see table 1. In the shake flask cultures the lowest eritadenine content was detected. In this case there is no impeller and hence the mycelia form macroscopic aggregates, pellets. The mycelial morphology in the bioreactor cultivations were freely dispersed filaments, and the eritadenine content were higher than in the shake flasks. In all cases the initial pH was 5.8, but during growth the pH dropped to 3.0 in the shake flasks. This low final pH indicates acid production. Further, in the cases where pH was uncontrolled, the final pH in the bio-reactors was 4.2 and 5.0 at 250 and 50 rpm, respectively. Clearly, the mycelia change their metabolism and acid production, depending on the physical culture conditions. According to previous studies (25) optimum pH for growth of shiitake mycelia is 3.0-3.5, while for production of antibacterial substances the optimum pH was 4.5. The low final pH in shake flasks combined with the relatively low amount of eritadenine indicate that for eritadenine production, a pH higher than 3.0 is preferable. Further, the results from the bioreactor cultivations indicate that lower pH than 5.7 favour eritadenine production, at the same stirring rate. When comparing the biomass produced, the higher agitation speed (250 rpm) runs resulted in about double the mycelial biomass than runs at lower (50 rpm) agitation speed, whereas eritadenine production was higher in the latter case. Taken together, the results from this study show that eritadenine is produced by shiitake mycelia and the major part of it is excreted to the surrounding medium. The results also indicate that the optimal conditions for mycelial biomass production and eritadenine production not necessarily coincide.

The following examples provided in table 1 are intended only to further illustrate the invention and are not intended to limit the scope of the invention. Thus, stirring rates or agitation speeds are only intended as examples. The stirring rates could vary from at least 25 to as high as is possible in order to producing eritadenine in liquid phase fermentation. The stirring rates depends on the size of the impeller. Thus, the skilled person in the field could optimize the method depending on the available equipment. Examples of stirring rates could then be; 25, 50, 100, 250, 500, 1000, 1500, 2000, 3000, 4000, 5000, 6000, and 7000. The preferred pH interval is in the order of 3.0 to 6.0. Other examples of intervals are 3.0-5.7, 3.5-5.7, 3.5-5,0, 4.0-5.0, etc.

One example of exposing *Lentinus edodes* to shear during its cultivation is stirring but other agitation techniques could be used. Any type of equipment such as a bioreactor could be used.

TABLE 1

Eritadenine content measured in the shiitake mycelia and culture broth from various submerged cultivations by HPLC analysis.

| | Eritadenine amounts | | |
|---|---|---|---|
| Cultivation conditions | In biomass (mg/g mycelia) | In broth (mg/g mycelia) | Total amount (mg/g mycelia) |
| Shake flask, 150 rpm, 23° C., no pH control | 0.64 | 5.91 | 6.55 |
| Bioreactor, 250 rpm, 25° C., pH 5.7 | 1.40 | 24.60 | 26.00 |
| Bioreactor, 250 rpm, 25° C., no pH control | 0.2 | 32.41 | 32.61 |
| Bioreactor, 50 rpm, 25° C., pH 5.7 | 0.36 | 33.46 | 33.82 |
| Bioreactor, 50 rpm, 25° C., no pH control | 0.10 | 39.43 | 39.53 |

EXAMPLES

Material and Methods

Fungal material. The shiitake strain used was *Lentinus edodes*-2 (Le-2). Mycelia of this strain were kindly supplied by Dr. Gary L. Mills, Diversified Natural Products, Inc., Scottville, Mich., USA. The mycelia were cultivated on malt yeast agar (MYA) plates composed of (w/v) 2% malt extract, 0.2% yeast extract and 2% microbial agar, for 10 days at 23° C.

Shake flask cultures. Mycelia from MYA plates were homogenised in a 0.05 mM phosphate buffer, pH 5.8, and transferred to 200 mL of malt-yeast medium composed of (w/v) 2% malt extract and 0.2% yeast extract, with 2% glucose added. The submerged cultivation took place in 500 mL shake flasks at 150 rpm for 20 days at 23° C. Following cultivation, the mycelia were harvested by filtering the culture through Whatman OOH filter paper and washed with distilled water. The biomass was then dried over night and the dry weight determined. The filtrated broth was collected for further analysis.

Bioreactor cultivation. Mycelia from MYA plates were homogenised in a 0.05 mM phosphate buffer, pH 5.8, and transferred to 700 mL malt-yeast medium composed of (w/v) 2% malt extract, 0.2% yeast extract, with 2% glucose added. The submerged cultivation took place in 1 L bioreactors (Biobundle 1 L, Applikon Biotechnology, the Netherlands) with a stirring rate of either 50 or 250 rpm, a temperature of 25° C., a dissolved oxygen flowrate of 1/vol/vol, and a pH either controlled at 5.7 or uncontrolled. After 20 days of cultivation the mycelia were harvested by filtering the culture through Whatman OOH filter paper and washed with distilled water. The biomass was then dried over night and the dry weight determined. The filtrated broth was collected for further analysis.

Preparation of eritadenine standard. Eritadenine was synthesized according to the following procedure. In the first step, methyl 2,3-O-Isopropylidene-β-D-ribofuranoside was synthesized (22). This product was further processed to give the compound methyl 2,3-O-isopropylidene-5-O-p-toluenesulfonyl-β-D-ribofuranoside (23). The third step was a reaction of sodium salt of adenine with methyl 2,3-O-Isopropylidene-5-O-p-toluenesulfonyl-β-D-ribofuranoside. This reaction gave the product methyl 5-(6-Aminopurin-9H-9-yl)-2,3-O-isopropylidene-5-deoxy-β-D-ribofuranoside. Hydrolysis of this product resulted in 5-(6-Aminopurin-9H-9-yl)-5-deoxy-D-ribofuranose. The final step was an air oxidation of the previous compound to get the product; 2(R),3

(R)-dihydroxy-4-(9-adenyl)-butyric acid, i.e. d-eritadenine (24). All chemicals were of analytical grade. In order to verify the correct product and its purity, NMR analysis was conducted for each step of the synthesis and compared with the literature. An LC/MS run further confirmed the final product. A stock solution (1.98 mg/mL) of the standard was prepared by dissolving synthesized eritadenine in distilled water.

Extraction of eritadenine from mycelia. The mycelial biomass was extracted with 80% (v/v) methanol for about 3 hours under reflux, with a solid-liquid ratio of 1:20. The fungal extract was then filtered through Whatman No. 5 filter paper and washed with distilled water. The resulting filtrate was concentrated in vacuo at 50-60° C. and analyzed.

Ion exchange purification of culture medium. The broth was concentrated in vacuo and the pH adjusted to 5.8 and applied to a column of Amberlite IR-120 ($H^+$) ion exchange resin. The substance was eluted with 2% ammonia, showing high absorbance at 260 nm. The volume collected was evaporated to dryness in vacuo at 50-60° C., diluted in 50 mL distilled water and applied to an Amberlite IRA-67 ($OH^-$) ion exchange resin. The substance was eluted with 0.1 M acetic acid and fractions showing high absorbance at 260 nm were collected. After evaporation to dryness in vacuo at 50-60° C. the mushroom sample was dissolved in distilled water and analyzed.

HPLC analysis. The eritadenine concentrations in shiitake mycelia and culture broth were analyzed by HPLC (Series 200 Quaternary LC pump and UV-VIS detector, TotalChrom software, PerkinElmer) and separated over a C18 column (RESTEK ultra aqueous, 5 µm, 4.6 mm×150 mm). Prior to analysis the samples were diluted twice with the initial mobile phase and filtered through a 0.2 µm syringe filter. The HPLC analysis was conducted at 23° C., with a flow rate of 1 mL/min and UV detection at 260 nm. The initial mobile phase was 0.05% TFA in aqueous solution: 0.05% TFA in MeCN, in the proportions 98:2 followed by a linear change to 40:60 over 10 min, and then returned to the initial condition for 15 min. All data were collected and processed using PerkinElmer's TotalChrom analytical software. Peak areas from the chromatograms were evaluated on the basis of a reference curve prepared from standard samples of eritadenine diluted in the initial mobile phase to concentrations in the range 0.0124-0.198 mg/mL.

REFERENCES

1. Kabir, Y.; Kimura, S., Dietary Mushrooms Reduce Blood-Pressure in Spontaneously Hypertensive Rats (Shr). J. Nutr. Sci. Vitaminol. 1989, 35, (1), 91-94.
2. Kabir, Y.; Yamaguchi, M.; Kimura, S., Effect of shiitake (*Lentinus edodes*) and maitake (*Grifola frondosa*) mushrooms on blood pressure and plasma lipids of spontaneously hypertensive rats. J. Nutr. Sci. Vitaminol. 1987, 33, (5), 341-346.
3. Kaneda, T.; Tokuda, S., Effect of various mushroom preparations on cholesterol levels in rats. J. Nutr. 1966, 90, 371-376.
4. Suzuki, S.; Ohshima, S., Influence of shiitake (*Lentinus edodes*) on human serum cholesterol. Mushroom Sci. 1974, 9, 463-467.
5. Chibata, I.; Okumura, K.; Takeyama, S.; Kotera, K., Lentinacin: a new hypocholesterolemic substance in *Lentinus edodes*. Experientia 1969, 25, 1237-1238.
6. Kamiya, T.; Saito, Y.; Hashimoto, M.; Seki, H., Structure and synthesis of lentysine, a new hypocholesterolemic substance. Tetrahedron Letters 1969, 10, 4729-4732.
7. Tokita, F.; Shibukawa, N.; Yasumoto, T.; Kaneda, T., Isolation and chemical structure of the plasma-cholesterol reducing substances from shiitake mushroom. Mushroom Sci. 1972, 8, 783-788.
8. Rokujo, T.; Kikuchi, H.; Tensho, A.; Tsukitani, Y.; Takenawa, T.; Yoshida, K.; Kamiya, T., Lentysine: a new hypolipidemic agent from a mushroom. Life Sci. 1970, 9, 379-385.
9. Shimada, Y.; Morita, T.; Sugiyama, K., Eritadenine-induced alterations of plasma lipoprotein lipid concentrations and phosphatidylcholine molecular species profile in rats fed cholesterol-free and cholesterol-enriched diets. Biosci. Biotechnol. Biochem. 2003, 67, 996-1006.
10. Shimada, Y.; Morita, T.; Sugiyama, K., Dietary eritadenine and ethanolamine depress fatty acid desaturase activities by increasing liver microsomal phosphatidylethanolamine in rats. J. Nutr. 2003, 133, 758-765.
11. Shimada, Y.; Yamakawa, A.; Morita, T.; Sugiyama, K., Effects of dietary eritadenine on the liver microsomal delta 6-desaturase activity and its mRNA in rats. Biosci. Biotechnol. Biochem. 2003, 67, 1258-1266.
12. Sugiyama, K.; Akachi, T.; Yamakawa, A., Eritadenine-induced alteration of hepatic phospholipid-metabolism in relation to its hypocholesterolemic action in rats. J. Nutr. Biochem. 1995, 6, 80-87.
13. Sugiyama, K.; Yamakawa, A.; Kawagishi, H.; Saeki, S., Dietary eritadenine modifies plasma phosphatidylcholine molecular species profile in rats fed different types of fat. J. Nutr. 1997, 127, 593-599.
14. Takashima, K.; Izumi, K.; Iwai, H.; Takeyama, S., The hypocholesterolemic action of eritadenine in the rat. Atherosclerosis. 1973, 17, 491-502.
15. Takashima, K.; Sato, C.; Sasaki, Y.; Morita, T.; Takeyama, S., Effect of eritadenine on cholesterol metabolism in the rat. Biochem. Pharmacol. 1974, 23, 433-438.
16. Votruba, I.; Holý, A., Eritadenine a novel type of potent inhibitors of S-adenosyl-L-homocysteine hydrolase. Collect. Czech. Chem. Commun. 1982, 47, 167-172.
17. Schanche, J.; Schanche, T.; Ueland, P.; Holy, A.; Votruba, I., The effect of aliphatic adenine analogues on S-adenosylhomocysteine and S-adenosylhomocysteine hydrolase in intact rat hepatocytes. Mol. Pharmacol. 1984, 26, 553-558.
18. Saito, M.; Yasumoto, T.; Kaneda, T., Quantitative analyses of eritadenine in shiitake mushroom and other edible fungi. J. Jap. Soc. Food Nutr. 1975, 28, 503-513.
19. Vitanyi, G.; Lelik, L.; Bihatsi-Karsai, E.; Lefler, J.; Nagy-Gasztonyi, M.; Vereczkey, G., Detection of eritadenine in extracts from shiitake mushroom by gas chromatography mass spectrometry. Rapid Commun. Mass Spectrom. 1998, 12, 120-122.
20. Enman, J.; Rova, U.; Berglund, K. A., Quantification of the bioactive compound eritadenine in selected strains of shiitake mushroom (*Lentinus edodes*). J. Agric. Food. Chem. 2007, 55, (4), 1177-1180.

21. Lelik, L.; Vitanyi, G.; Lefler, J.; Hegoczky, J.; Nagy-Gasztonyi, M.; Vereczkey, G., Production of the mycelium of shiitake (*Lentinus edodes*) mushroom and investigation of its bioactive compounds. Acta Alimentaria 1997, 26, 271-277.
22. Leonard, N. J.; Carraway, K. L., 5-amino-5-deoxyribose derivatives. Synthesis and use in the preparation of reversed nucleosides. J. Heterocycl. Chem. 1966, 3, 485-489.
23. Levene, P. A.; Stiller, E. T., Acetone Derivatives of d-Ribose. J. Biol. Chem. 1934, 106, 421-429.
24. Kawazu, M.; Kanno, T.; Yamamura, S.; Mizoguchi, T.; Saito, S., Studies on the oxidation of "reversed nucleosides" in oxygen. I. Synthesis of eritadenine and its derivatives. J. Org. Chem. 1973, 38, 2887-90.
25. Hassegawa, R. H.; Kasuya, M. C. M.; Vanetti, M. C. D., Growth and antibacterial activity of Lentinula edodes in liquid media supplemented with agricultural wastes. Electr. J. Biotech. 2005, 8, 212-217.

The invention claimed is:

1. A method for producing eritadenine in liquid phase fermentation of *Lentinus edodes*, comprising
    culturing the *Lentinus edodes* in a liquid culture medium, and exposing it to shear during its cultivation, and
    isolating eritadenine that is secreted into the culture medium.
2. The method according to claim 1 wherein the shear is achieved by stirring the *Lentinus edodes* at a stirring rate of at least 25 rpm.
3. The method according to claim 1 wherein the pH of the culture medium is in the range of about 3.0-6.0.
4. The method according to claim 3 wherein the pH of the culture medium is in the range of about 4.0-5.0.
5. The method according to claim 2 wherein the pH of the culture medium is in the range of about 3.0-6.0.
6. The method according to claim 5 wherein the pH of the culture medium is in the range of about 4.0-5.0.

* * * * *